(12) United States Patent
Noll et al.

(10) Patent No.: US 7,553,664 B2
(45) Date of Patent: Jun. 30, 2009

(54) THREE-DIMENSIONAL SKIN MODEL

(75) Inventors: Michaela Noll, Stuttgart (DE); Thomas Graeve, Stuttgart (DE)

(73) Assignee: Fraunhofer-Gesellschaft zur Forderung der angewandten Forschung e.V. (DE)

( * ) Notice: Subject to any disclaimer, the term of this patent is extended or adjusted under 35 U.S.C. 154(b) by 401 days.

(21) Appl. No.: 10/296,967

(22) PCT Filed: May 29, 2001

(86) PCT No.: PCT/EP01/06074

§ 371 (c)(1),
(2), (4) Date: Jul. 17, 2003

(87) PCT Pub. No.: WO01/92477

PCT Pub. Date: Dec. 6, 2001

(65) Prior Publication Data

US 2004/0018149 A1 Jan. 29, 2004

(30) Foreign Application Priority Data

May 31, 2000 (DE) ................. 100 26 789
Dec. 15, 2000 (DE) ................. 100 62 623

(51) Int. Cl.
*C12N 5/00* (2006.01)
*C12N 5/02* (2006.01)

(52) U.S. Cl. ................. 435/378; 435/325; 435/373; 435/393; 435/395

(58) Field of Classification Search ................. 435/371, 435/373, 393, 395, 325, 387; 424/400, 422, 424/572, 439, 535, 725, 93.7
See application file for complete search history.

(56) References Cited

U.S. PATENT DOCUMENTS 5,946,101 A * 8/1999 Kobayashi ................. 356/613

FOREIGN PATENT DOCUMENTS

| WO | WO 95/33821 A1 | 12/1995 |
| WO | WO 98/17791 A1 | 4/1998 |
| WO | 197 21 661 A1 | 11/1998 |
| WO | WO 99/00152 A2 | 1/1999 |
| WO | WO 99/08728 A1 | 2/1999 |

OTHER PUBLICATIONS

Yang et al., "Tissue engineered artificial skin composed of dermis and epidermis", Artificial Organs, Jan. 2000, 24(1):7-17.*
O'Keefe et al., "Production of Fibronectin by Epithelium in a Skin Equivalent", J Invest Dermatol, May 1987; 88(5):634-639.*
Stark, et al., "Organotypic Keratinocyte Cocultures in Defined Medium with Regular Epidermal Morphogenesis and Differentiation." The Journal of Investigative Dermatology; vol. 112, No. 5, May 1999, pp. 681-691.
Mio, et al., "Regulation of Fibroblast Proliferation in Three-Dimensional Collagen Gel Matrix." In Vitro Cell. Dev. Biol.-Animal; 32:427-433, Jul./Aug. 1996.
Ulreich, et al., "Chondrocytes Maintain Their Phenotype when Cultured on a Three Dimensional Collagen Matrix". Department of Surgery, University of Arizona Medical Center, Tucson, AZ 85724. Schuman et al., Biomaterials, vol. 16, pp. 809-814 (1995).

* cited by examiner

*Primary Examiner*—Ruth A Davis
(74) *Attorney, Agent, or Firm*—Dickstein, Shapiro, LLP.

(57) ABSTRACT

The present invention relates to methods for cultivating dermal fibroblasts, methods for preparing in vitro dermis equivalents, methods for preparing three-dimensional in vitro skin equivalents, an in vitro dermis equivalent, a three-dimensional in vitro skin equivalent, and methods for determining the effect of a chemical substance or of an agent on human skin cells using the in vitro dermis equivalent and/or the in vitro skin equivalent.

11 Claims, 6 Drawing Sheets

THREE-DIMENSIONAL SKIN MODEL

FIELD OF THE INVENTION

The invention relates to a skin-specific, three-dimensional, preferably human, in vitro skin consisting of a dermis equivalent and an epidermis equivalent, as well as a method for preparing, cultivating, and using this skin equivalent and its components.

BACKGROUND OF THE INVENTION

Skin-specific full skin models, also called in vitro skin equivalents, can be used in particular in dermatology and allergiology as a test skin in order to test substances, for example, potential medications or cosmetics, or agents such as light and heat, for their pharmacological effects, in particular irritation, toxicity, and inflammation effects, as well as their compatibility. Such a system also can be used to answer many types of immunological, histological, and molecular-biological questions. This includes, for example, studies of wound healing and of the penetration and absorption of substances. Compared with animal experiments and studies using human test subjects, the studies or tests of substances with such full skin models offer substantial advantages since the results obtained with them are more reproducible and the studies are less costly and quicker.

In recent years, mostly human cell cultures have been used as in vitro systems for the testing of raw materials and products. A further development in cell culture technology are three-dimensional, organ-like human cell structures and co-culture systems. The results obtained with these can be transferred to humans even better than the results obtained with single cell cultures. The developments by Rheinwald and Green (Rheinwald, J. G. et al., "Serial cultivation of strains of human epidermal keratinocytes: The formation of keratinizing colonies from single cells", Cell, 6 (1975), 331-344; Green, H. et al., "Growth of cultured human epidermal cells into multiple epithelia suitable for grafting", Proc. Nat. Acad. Sci. USA 76 (1979), 5665-5668) were the start of the cultivation of human keratinocytes and their use in burn medicine and in vitro dermatology. In the past, different models of reconstructed skin have been produced in vitro.

EP 0 197 090 B1 discloses a method for forming a skin equivalent, wherein a hydrated collagen network is produced by mixing an acidic collagen solution with contractile cells, for example, fibroblasts. After neutralizing the pH value, collagen fibrils are precipitated in the collagen network. The contractile cells attach to the collagen network and bring about its contraction, whereupon a dermis equivalent forms. By introducing punch biopsy skin samples into the collagen network, keratinocytes from the punch biopsy samples are able to grow on the surface of the dermis equivalent, whereupon a skin equivalent forms.

EP 0 285 474 B1 discloses a skin equivalent comprising a dermis equivalent obtained from collagen and fibroblasts, as well as a multilayer epidermis equivalent. The dermis equivalent is hereby inoculated with a human or animal explant, for example, a hair follicle, in order to obtain the epidermis equivalent.

EP 0 020 753 B1 describes a method for forming tissue, especially skin tissue, wherein fibroblasts are introduced into a hydrated collagen network also, and a tissue forms after the collagen network contracts. Keratinocytes previously cultivated in vitro or keratinocytes extracted from foreskin can be applied to this tissue, whereupon a skin replacement is formed.

EP 0 418 035 B1 discloses a tissue equivalent comprising a hydrated collagen network contracted with a contractile agent, such as fibroblasts, and a collagen gel that is in contact with a permeable element. The mixture of collagen and contractile agent is applied to the collagen gel, whereby the contact between collagen gel and permeable element, for example, a polycarbonate membrane, interrupts the radial or lateral contraction of the collagen network so that the network only contracts with respect to its thickness. After the dermis equivalent forms, keratinocytes can be seeded, whereupon a skin equivalent forms.

U.S. Pat. No. 5,861,153 furthermore forms a skin equivalent consisting of an epidermis equivalent on a carrier, whereby the epidermis equivalent comprises keratinocytes and induced or non-induced precursors of Langerhans cells.

The carrier may be a collagen network containing fibroblasts or dermis sections from which the epidermis has been removed, artificial membranes, a subcutaneous replacement based on collagen, or synthetic materials.

U.S. Pat. No. 4,963,489 describes stroma tissue prepared in vitro, whereby the stroma cells, for example, fibroblasts, envelop a basic network consisting of a biocompatible material, for example, cellulose. The described system can be used, for example, to produce a three-dimensional skin culture system, whereby keratinocytes and melanocytes are applied to the dermis equivalent, i.e., the three-dimensional stroma carrier matrix.

U.S. Pat. No. 5,755,814 describes a skin model system that can be used both as an in vitro test system and for therapeutic purposes. The system comprises a three-dimensional, networked matrix of insoluble collagen that contains fibroblasts and stratified layers of differentiated epidermis cells, whereby an epidermis cell layer is in direct contact with the surface of the collagen matrix. The networking of the matrix can be achieved both using a thermal treatment with water removal, as well as by chemical means, for example, with carbodiimide.

U.S. Pat. No. 5,882,248 describes a method for determining the effects of chemical substances or agents on a human skin model system according to U.S. Pat. No. 5,755,814. The interaction between the skin model system and the substances to be tested is determined with the help of the release of substances by cells of the skin model system as well as with the effects on metabolism, proliferation, differentiation, and reorganization of these cells.

WO 95/10600 furthermore describes a method with which an epidermis equivalent can be obtained. This epidermis equivalent can be used for pharmaceutical and/or cosmetic sun tanning tests.

BRIEF SUMMARY OF THE INVENTION

The advantage of known skin models is that they consist in most cases only of one or several epidermal layer(s) of keratinocytes. In those cases where a stratified epidermis is obtained, tissue explants are used that have an inherent risk of contamination with pathogens, which may result in falsified results when the skin equivalent is used at a later time as a test skin. To the extent that the described skin models have a dermal part, the latter often consists of spongy, cross-linked material that, in addition to collagen, also may contain other non-skin-specific materials. If the dermal part in the skin equivalents described in the prior art consists only of collagen and fibroblasts, it is subject to an undefined shrinkage process that can be attributed to a severe shrinking of the collagen gel and an emission of fluid from it. As a result, the skin equivalents described in the state of the art are only suitable to a limited extent as a test skin with a defined size, and the results obtained with them can only be transferred to a limited extent to native human skin.

The technical objective of the present invention therefore is to provide a three-dimensional, human, in vitro full skin model, which substantially corresponds to native human skin, as well as methods and means for its production, and which has both an epidermis layer as well as a dermis layer that is not subject to a shrinkage process, and which can be used as a test skin of a defined size, for example, for the study of pharmacological and cosmetic effects.

The invention realizes this underlying objective by providing a method for the differentiation and/or multiplication of extracted dermal fibroblasts, whereby the fibroblasts are cultivated in a three-dimensional, gel-like biomatrix and are able to multiply therein. In addition to the fibroblasts to be cultivated, this biomatrix contains a network of human or animal collagen constituted from a collagen solution, i.e., tissue-specific matrix proteins. According to the invention, this collagen-fibroblast gel preferably is subjected to a one- to two-day submerse culture. Then keratinocyte stem cells are seeded onto the fibroblast-containing biomatrix. In an especially preferred embodiment, preferably keratinocytes with a comparatively high content, for example, 0.5%, 1%, 2%, 5%, 8%, or 10% of the keratinocyte cell population, or including only undifferentiated stem cells, are used. Using specific culture conditions, including a multi-day submerse culture and subsequent multi-day airlift culture of the biomatrix system, as well as specific culture media, the keratinocytes undergo a differentiation to a multilayer epidermis layer. According to the invention, a preferred embodiment furthermore provides that before, during, or after the seeding of the keratinocytes, other cell types and/or other cells of other tissue types, for example, immune system cells, also can be seeded on the biomatrix.

The methods according to the invention therefore make it possible to obtain an organoid in vitro skin model that is constructed of two tissue-specific layers, i.e., a dermis equivalent and an epidermis equivalent. The organo-specific skin model both histologically as well as functionally corresponds substantially to native skin.

With the help of a special method for the collagen extraction and the composition of the collagen suspension used to form the biomatrix, it is made possible that the dermis equivalent is not subject to any shrinkage process during the course of the cultivation period. Based on the culture methods used and the use of a cell culture insert with a special surface coating, it is achieved that the dermal part is only subjected to defined shrinkage in vertical direction, while shrinkage in a horizontal direction is prevented. As a result, skin equivalents with a defined diameter, uniform surface, and defined termination with respect to the edge of the culture insert, are obtained. In tests of substances for pharmacological and/or cosmetic effects, the uniform size and uniform properties of the full skin model used as a test surface permit higher quality results and more reproducible test results.

An especially preferred embodiment of the invention comprises the cultivation of dermal fibroblasts in a three-dimensional biomatrix in order to multiply the fibroblasts or to produce a dermis equivalent and/or skin equivalent.

In connection with the present invention, the term "cultivation of cells" means a preferably in vitro maintenance of the life functions of cells, for example, fibroblasts, in a suitable environment, for example, by adding and removing metabolic educts and products, in particular also a multiplication of the cells.

In connection with the present invention, the term "dermal fibroblasts" means naturally occurring fibroblasts, especially occurring in the dermis, or genetically engineered fibroblasts or their precursors. Fibroblasts are the precursors of dermal fibrocytes, i.e., spindle-shaped cells of the dermal connective tissue with an oval nucleus and long appendices. The fibroblasts may be of animal or human origin.

The biomatrix intended for cultivating the fibroblasts thus contains the fibroblasts to be cultivated as well as a collagen network, newly constituted from a preferably fresh collagen solution of human or animal origin, with a concentration of at least 3 mg of collagen per ml of biomatrix, preferably 3.5 to 4.5 mg of collagen per ml of biomatrix. The collagen network is obtained from a preferably cell-free, acidic solution of collagen I, whereby the protein concentration of the collagen solution is preferably 5 to 7 mg/ml. The pH value of the collagen solution is 0.1 to 6.9, preferably 2.0 to 5.0, especially 3.0 to 4.5, in particular 3.2 to 4.2, and especially preferably 3.8. In order to prepare the fibroblast-containing biomatrix according to the invention, a solution containing a preferably 5× concentrated cell culture medium, preferably 5× concentrated M199 cell culture medium, buffer, preferably HEPES buffer, serum, preferably fetal calf serum (FCS), and chondroitin-(4/6)-sulfate, and preferably $1.5 \times 10^5$/ml fibroblasts, in particular precultivated fibroblasts, is added to the collagen solution at 2° C. to 10° C., preferably at 4° C., and is well mixed. This mixture is placed into the wells of a microtiter plate with 24 wells, whereby each well has a diameter of 10 mm, and is then gelled by increasing the temperature to, for example, room temperature or 37° C. After gelling the fibroblast collagen gels, fibronectin, preferably human fibronectin, is placed on top of the gels. Fibronectins are structural or adhesion proteins produced in fibroblasts, whose in vivo function is the binding to other macromolecules, for example, collagen, and adhesion of cells to adjoining cells. This means that by adding fibronectins to the fibroblast collagen matrix, the binding of the fibroblasts both to collagen and to each other is promoted. Subsequent cultivation of the fibroblasts in the collagen gel preferably takes place in submerse culture. In connection with the present invention, a "submerse cultivation or "submerse culture" means a method for cultivation cells in which the cells are covered with a nutrient solution. The biomatrix containing fibroblasts thus is coated with cell culture medium and incubated at 37° C.

In an advantageous embodiment of the invention, the fibroblasts cultivated in the biomatrix may be removed again from the biomatrix and may be potentially reintroduced into a biomatrix, whereby the cells do not lose their specific metabolic actions and their differentiation status. The method according to the invention thus makes it possible to perform an intermediate cultivation of the fibroblasts in the biomatrix. The method according to the invention thus has the advantage that sufficient cell material for the preparation of dermis equivalents and/or skin equivalents can be made available with a smaller starting amount of fibroblasts.

Another advantageous embodiment of the invention provides that dermal fibroblasts to be tested with respect to their function, morphology and/or differentiation status are introduced into a previously mentioned, three-dimensional biomatrix, cultivated, and simultaneously and/or subsequently tested. The invention therefore also relates to screening and diagnostic procedures performed using dermal fibroblasts, whereby the fibroblasts are cultivated according to the previously described method and may be tested simultaneously and/or subsequently, for example, for pharmacological, toxicological, physiological, morphological and/or molecular-biological parameters.

In another advantageous embodiment of the invention, the dermal fibroblasts are cultivated in the three-dimensional biomatrix, as previously described, in such a way that subsequently a dermis equivalent can be obtained. In connection with the present invention, the term "dermis equivalent" means a connective-tissue-like layer of collagen and fibroblasts that substantially corresponds to the native dermis.

The dermis equivalent obtained in this way may be used for screening and diagnostic procedures, in particular for studying the effects of chemical substances, for example, potential medications, or components of cosmetics, or other agents. In connection with the present invention, the term "agent" or "agents" means in particular physical means, such as light, heat, etc., acting on the skin or skin cells. The invention therefore also relates to screening and diagnosis procedures using the dermis equivalents prepared according to the invention.

A preferred embodiment of the invention comprises the treatment of the dermis equivalent in the presence and absence of the substance to be studied and/or the agent to be studied, and the comparison of the observed effects on the cells or cell components of the dermis equivalent.

Another preferred embodiment of the invention comprises a method for studying the penetration of substances using the dermis equivalent prepared according to the invention and using a skin equivalent according to the invention, which consists of a dermis equivalent and an epidermis equivalent.

An especially preferred embodiment of the invention also relates to a previously mentioned method for cultivating dermal fibroblasts in a biomatrix in order to prepare a skin equivalent consisting of dermis equivalent and epidermis equivalent. One to two days, preferably two days, after the previously described preparation and incubation of the collagen fibroblasts gels, keratinocytes are seeded on the gel in this process.

In connection with the present invention, the term "keratinocytes" means cells of the epidermis that form keratinizing squamous epithelium, or genetically engineered keratinocytes, or their prescursors, which may be of animal or human origin. Since the formation of a well-differentiated epidermis with intact keratinization depends extensively on the content of basal stem cells in the used keratinocytes, the keratinocytes seeded on the collagen gel thus, if possible, are preferably undifferentiated keratinocyte stem cells from human biopsy tissue, i.e., cytokeratin-19- or integrin-β1-positive basal stem cells. These are preferably precultivated cells, especially preferably keratinocytes in the first or second cell passage. The seeding of the keratinocytes on the biomatrix preferably takes place in a cell culture medium, especially preferably in KBM medium (Clonetics) that contains 5% fetal calf serum. The biomatrix is then coated with KBM medium containing human epidermal growth factor (hEGF) (0.1 µg/500 ml medium), BPE (15 mg/500 ml medium) and 0.8 mM $CaCl_2$ and preferably undergoes a 1- to 3-day submerse cultivation. A complete differentiation of the keratinocyte layers is achieved with an airlift culture with KBM medium containing 1.8 mM $CaCl_2$ and without hEGF and BPE. In connection with the present invention, an "airlift culture" means a culture in which the height of the nutrient medium level is exactly adapted to the height of the biomatrix, while the keratinocytes or the cell layers formed by the keratinocytes are above the nutrient medium level and are not covered by the nutrient medium, i.e., the cultivation takes place at the air/nutrient medium interface, whereby the cultures are supplied with nutrients from the bottom. For this, the inserts are transferred from the microtiter plate with 24 wells into the wells of a microtiter plate with 6 wells, each of which has a diameter of 3.5 cm. After a preferably 12- to 14-day airlift culture, a skin-specific in vitro full skin model that consists dermis equivalent and epidermis equivalent develops.

The method according to the invention for preparing an in vitro full skin model advantageously can be modified in such a way that prior to, during, or following the seeding of keratinocytes other skin cell types, such as melanocytes, immune cells and/or endothelial cells can be seeded onto the biomatrix and further cultivated.

The invention therefore also relates to a skin-specific in vitro full skin test model, in particular a human or animal in vitro full skin test model, that was prepared according to the method according to the invention and a potential, following and/or preceding standard type cultivation process and that comprises at least 2 to 4 proliferative, several differentiating, and at least 4 to 5 keratinized cell layers, whereby the epidermis equivalent comprises the stratum basale, stratum spinosum, stratum granulosum, and stratum corneum, and whereby a functional basal membrane of matrix proteins is contained between the dermis equivalent and the epidermis equivalent, and whereby in addition skin-specific proteins, such as fillgrin, Ki-67, and cytokeratin 10 are expressed.

As a result of the complexity of the prepared skin model, it may be used to solve different questions of the chemical-pharmaceutical industry and cosmetic industry. The skin equivalent prepared according to the invention is particularly suitable for product testing, for example, with respect to the efficacy, adverse side effects, for example, irritation, toxicity, and inflammatory effects or allergy-triggering effects, or the compatibility of substances. These may be substances intended for potential use as medications, especially dermatics, or substances that are components of cosmetics. The skin equivalent prepared according to the invention, for example, also may be used for studies of the absorption, transport and/or penetration of substances. It is also suitable for studying other agents, such as light and heat, for example, to study phototoxicity, i.e., the harmful effect of light with different wavelengths on cell structures. The skin equivalent prepared according to the invention naturally also can be used to study wound healing.

The effects of substances or agents on the human skin may be determined, for example, with the help of the release of substances, for example, cytokines or mediators, by cells of the skin model system, as well as the effects on gene expression, metabolism, proliferation, differentiation, and reorganization of these cells. By using methods for quantifying the cell damage, in particular by using a vital stain, such as a tetrazolium derivative, cytotoxic effects on skins cells can be demonstrated, for example. The tests of substances or agents in the human skin equivalent may include both histological as well as immunological and/or molecular-biological methods.

A preferred embodiment of the invention therefore comprises methods for studying the effect, especially of the pharmacological effects, of substances and agents on the human skin using the human skin equivalent prepared according to the invention. In an especially preferred embodiment, an EZ4U test is performed. EZ4U is a non-toxic, water-soluble, yellow tetrazolium salt that can be reduced by living cells into intensively colored formazanes. The reduction requires intact mitochondria, and the test therefore can be used to determine the vitality of cells.

Another preferred embodiment of the invention comprises a method for studying the penetration of substances, whereby both a dermis equivalent prepared according to the invention as well as a skin equivalent prepared according to the invention are treated with the substances to be studied, and the results obtained with the two systems are compared with each other.

In an especially preferred embodiment of the invention, the effects of chemical substances or other agents on special skin types are studied. Hereby cells of defined skin types, for example, skin types with few pigments and/or skin types with many pigments are used to establish skin equivalents according to the invention, and these are then tested with respect to the effect of substances or agents.

In another especially preferred embodiment of the invention, the skin equivalent prepared according to the invention is used as a model system for studying skin diseases and for developing new treatment options for skin disorders. Cell lines from patient with a certain skin disease can be used, for example, to establish patient-specific skin model systems and use them to study and evaluate the effectiveness of certain therapies and/or medications.

The invention also relates to a preferably gel-like biomatrix in which the previously mentioned cultivation methods can be performed, i.e., a biomatrix with dermal fibroblasts. The combination according to the invention of biomatrix and the dermal fibroblasts cultivated in it can be used, as previously described, to prepare a dermis equivalent and/or an organoid full skin model.

The term "biomatrix" stands for a gel structure that contains collagen, cell culture medium, serum, and buffer, for example, HEPES buffer. The collagen solution used for preparing the biomatrix is a solution with a high content of non-denatured, native collagen in an acidic, aqueous medium, preferably with a pH value of 3.8, for example, in acetic acid, preferably in 0.1% acetic acid solution. A high content of non-denatured collagen means a total collagen content in the solution of $\geq 50\%$, in particular $\geq 60\%$, $\geq 70\%$, $\geq 80\%$, $\geq 90\%$, or $\geq 95\%$, preferably $\geq 99\%$. In a preferred embodiment, no lyophilized collagen is used for this. The collagen content of the solution is preferably 3 mg of collagen per ml of solution to 8 mg of collagen per ml of solution, more preferably 5 mg of collagen per ml of solution to 7 mg of collagen per ml of solution, most preferably 6 mg of collagen per ml solution. It is preferred that collagen is used for this, which, after extraction, for example, from rat tails, is incubated in 0.1% acetic acid for 3 to 14 days at 4° C. with stirring, and whereby non-dissolved collagen parts are centrifuged off. Preferred cell culture media are DMEM (Dulbecco's Modified Eagle Medium) and M199. However, it is possible to use any desired cell culture medium that permits the cultivation of fibroblasts. It is preferred that for the serum a fetal calf serum (FCS) is used, and for the buffer, for example, HEPES buffer. The pH value of the solution of cell culture medium, buffer, and serum in the preferred embodiment is 7.5 to 8.5, for example, 7.6 to 8.2, in particular 7.8. Naturally, the biomatrix may contain further factors, for example, growth factors, adhesives, antibiotics, selection agents, etc.

The invention therefore also relates to methods for preparing a biomatrix that contains dermal fibroblasts, whereby in a first step fresh collagen of human or animal origin, for example, from rat tails, is prepared by collecting collagen fibers extracted from collagen-containing tissue in buffer solution, superficially disinfecting them in alcohol, and then washing them in buffer solution and transferring them into an acidic solution with a pH value of 0.1 to 6.9, preferably 2.0 to 5.0, especially preferably 3.0 to 4.0, in particular 3.3, for example, a 0.1% acetic acid solution. In a further step, the collagen in the solution is stirred at 2 to 10° C., in particular 4° C., for several days, for example, for 3 to 14 days, the non-dissolved collagen parts are centrifuged off, and a collagen solution with a collagen content of 3 mg/ml to 8 mg/ml is stored at 2 to 10° C., for example at 4° C. It is naturally also possible to temporarily store the solution in a frozen state, for example at −10° C. to −80° C., in particular at −20° C. To prepare the fibroblast-containing biomatrix according to the invention, a solution consisting of a preferably five times concentrated cell culture medium, serum, and buffer is mixed in a third step with precultivated and centrifuged-off fibroblasts, using preferably $1 \times 10^5$ to $2 \times 10^5$ cells per ml, preferably $1.5 \times 10^5$ cells per ml. This solution, or suspension, with a pH value from 7.5 to 8.5, preferably 7.6 to 8.2, in particular 7.8, is then mixed, for example, in a ratio of 1:2, with the previously mentioned collagen solution at 2 to 10° C., in particular at 4° C. The gel solution is then pipetted into culture containers and is coated, after gelling at 37° C., with medium. The biomatrix is then cultivated for at least two days, after which time keratinocytes can be applied to it.

Other advantageous embodiments of the invention are derived from the specification.

The invention is described in more detail using the following figures and examples.

DETAILED DESCRIPTION OF THE INVENTION

Example 1

Figure 1:
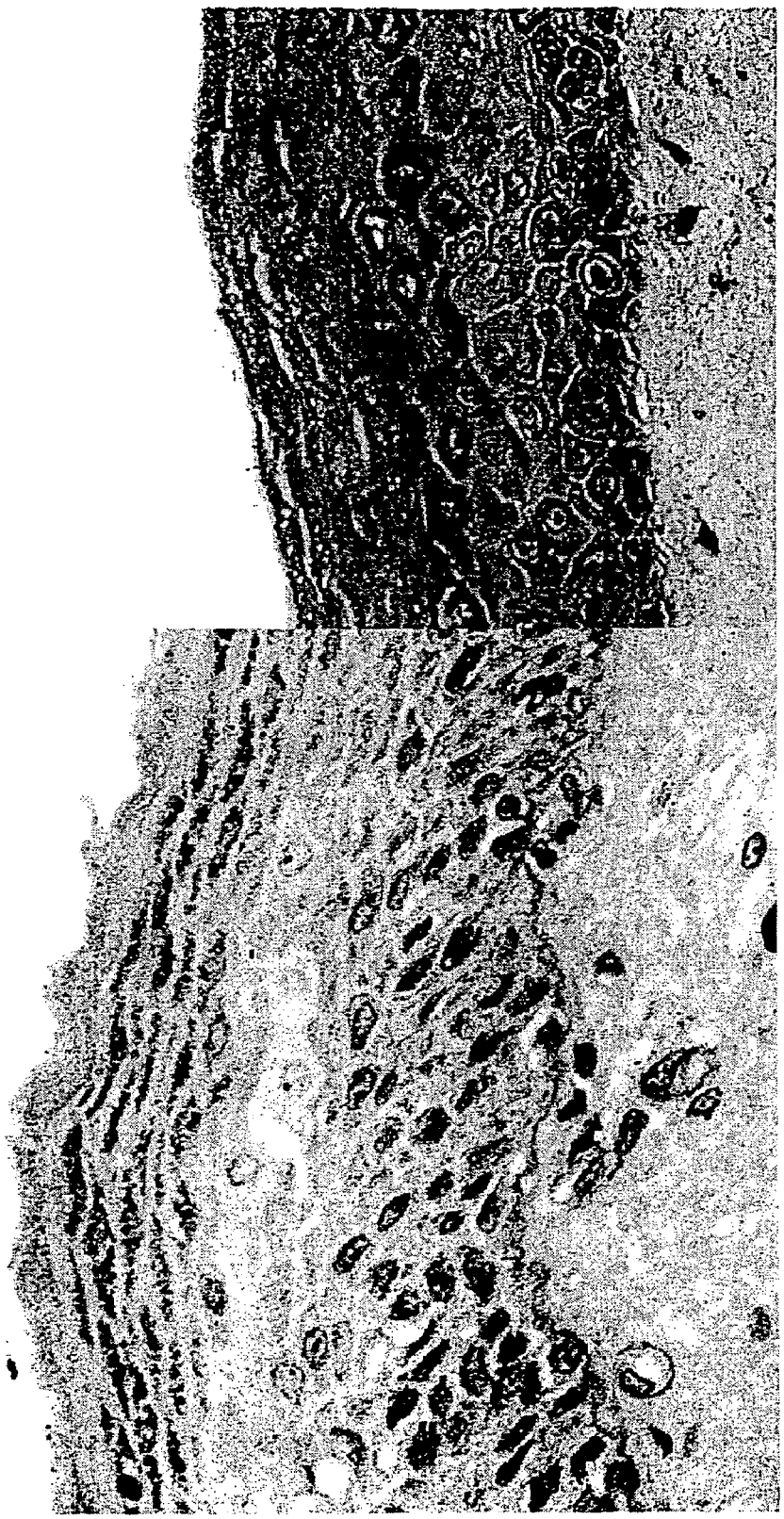
FIG. 1 shows a longitudinal section of native human skin and a longitudinal section of a human skin equivalent prepared according to the invention.

Preparation of a Three-Dimensional Human Skin Equivalent

Preparation of a Gel Solution 20 parts of 5× concentrated M 199 cell culture medium (Life Technologies), 10 parts of HEPES buffer (4.76 g in 100 ml PBS solution, pH value 7.3), and 1 part chondroitin-(4,6)-sulfate (5 mg/ml in PBS) are mixed, and the pH value of the mixture is adjusted to 7.8. The mixture is sterilized by filtration, after which 10 parts of fetal calf serum are added.

Preparation of a Collagen Solution

Collagen-containing tissue, for example, tendons from rat tails, is used to prepare a collagen solution. All work is performed under sterile conditions with sterile materials. After storage at −20° C., the rat tails are superficially disinfected with 70% alcohol. The rat tails are skinned, and the individual collagen fibers are extracted. If using other starting tissues, any possibly present cells may be carefully removed with a mechanical, enzymatic, or chemical treatment. The collagen fibers are collected in phosphate-buffered saline (PBS) (pH 7.2), superficially disinfected in 70% alcohol for 10 minutes, and then washed thoroughly with PBS. The weight of the fibers is determined, and the fibers are transferred into a 0.1% acetic acid solution (final concentration of approximately 8 to 12 mg/ml). This preparation is stirred for a period of about 3 to 14 days at 4° C., and any undissolved collagen parts are then removed using centrifugation (1,000 rpm, 1 hour, 8° C.). As a result, the collagen is dissolved, and is no longer in fiber, network or matrix form.

Preparation of the Collagen Gels Containing the Dermal Fibroblasts (Preparation for 24 Inserts)

16 ml of collagen solution are added into a 50 ml centrifuge tube and placed on ice. Precultivated, dermal fibroblasts are harvested and counted. $1.2 \times 10^6$ fibroblasts are placed into 8 ml of ice-cold gel solution, are well suspended, and added to the collagen solution without any air bubbles. Gel solution and fibroblasts are well mixed. 600 μl each of the mixture are carefully poured into the well of a 24-well microtiter plate (diameter of 10 mm per well). The mixture is gelled by a two-minute incubation at 37° C. After gelling the mixture, 50 μl each of fibronectin (5 μg/ml) are placed on each insert. Following a 10-minute incubation at 37° C. or a 30-minute incubation at room temperature, 1 ml of M199 medium is added for each well, whereby the inserts are coated with the medium. The fibroblasts contained in the gel undergo this submerse cultivation for 1 to 2 days at 37° C., whereby the medium is replaced with fresh medium every 12 hours.

Seeding of the Keratinocytes and Cultivation of the Skin Equivalents

Prior to seeding the keratinocytes, the medium is first carefully aspirated from the wells of the microtiter plate and from the gels. Then 500 μl of KBM medium (Clonetics) that contains 5% FCS is added for each well. The gels are coated with 50 μl of fibronectin solution each and are incubated for 1 hour at 37° C. Then 100,000 keratinocytes in 50-100 μl of KBM medium that contains 5% FCS are seeded for each gel and are incubated for 1 to 2 hours at 37° C. Then 500 μl KBM medium that contains 5% FCS, 8 mM $CaCl_2$, hEGF (0.1 μg/500 ml medium) and BPE (15 mg/500 ml medium) is added, and the gels undergo a submerse cultivation for 1 to 3 days, whereby the medium is replaced daily with fresh medium. The gels then each undergo another submerse cultivation for another 2 to 3 days in 1 to 1.5 ml of KBM medium that contains 2% FCS, 8 mM $CaCl_2$, hEGF, and BPE. The gels then undergo an airlift cultivation with the developing skin equivalent. For this purpose, the gels are transferred to a plate with 6 wells, and 1.5 to 2 ml of KBM medium with a $CaCl_2$ content of 1.88 mM, without hEGF and BPE, are added for each well, whereby the level of the medium is exactly adapted to the height of the gel, while the keratinocytes or the layers formed by the keratinocytes are not covered by the medium. The airlift cultivation is continued for at least 12 to 14 days.

FIG. 1 shows a comparison of native human skin and a human skin equivalent according to the invention.

Example 2

Testing of Chemical Substances on a Three-Dimensional Human Skin Equivalent

Substances samples were used equivalently for testing on the human skin equivalent. The objective was to study any irritating effect of the samples on the full skin model after 48 hours of incubation time via the EZ4U metabolism. The secretion of Il1α and $PGE_2$ was supposed to be determined in the media supernatants after 24 hours and after 48 hours by ELISA. Different concentrations of SDS were also run as a reference substance. Finally, all tested skin equivalents were fixed, and the morphological structure was tested and evaluated with stained paraffin sections.

For the SDS used as a reference substance, the exposure time (Et50) was determined from 1% SDS and the Ec50 concentrations over 24 hours or 48 hours of incubation time.

The skin equivalents each were prepared in a 6-well with 1 ml of medium (KBM without hEGF, without BPE, and with 1.8 mM $CaCl_2$). The samples were incubated on the surface of the corresponding skin models according to the following schedule:

Day 1: Application of 3 μl substance in the morning and in the afternoon.

Day 2: Media replacement and freezing of media supernatants for Il1α und $PGE_2$ determination. Treatment with 3 μl substance in the morning and in the afternoon.

Day 3: Freezing of media supernatants for Il1α und $PGE_2$ determination. Determination of cell metabolism in EZ4U test over a period of 2 hours. Fixation of slides and preparation of stained paraffin sections for histological evaluation.

The negative controls that were also run were treated correspondingly with 3 μl PBS. The reference substance or positive control used was SDS in different concentrations (0.01%, 0.05%, 0.1%, 0.5%, 1%). Duplicates were prepared for all samples.

The EZ4U test was performed as followed: After 48 hours of incubation, the cell metabolism of the individual skin equivalents was determined photometrically using a vital stain (tetrazolium derivative). All equivalents were washed carefully three times with 1.5 ml of PBS before performing the EZ4U test. Turnover kinetics of the negative controls, positive controls, and the equivalents treated with the samples were recorded over a period of 2 hours at 450 nm (with a reference wavelength of 620 nm). As already described, 750 ml of assay medium and 75 μl of dye per insert were incubated at 37° C. for this purpose. Both Ec50 and Et50 were determined for SDS. Et50 was determined according to different exposure times from 1% SDS (3 sec, 30 sec, 60 sec, 5 min, 15 min).

The Il1α and $PGE_2$ content in the media supernatants was determined after 24 hours and 48 hours of incubation of the samples using commercially available ELISA test kits and following their instructions.

The skin equivalents were histologically examined, whereby the slides were fixed in Bouin's solution and embedded in paraffin, histological sections were prepared and stained.

The cell metabolism of negative control, reference or positive control, and sample equivalents was determined by calculating the extinction differential (ΔOD). The change of the ΔOD by the reference standard in different concentrations and by 48-hour incubation of the samples was converted into percentages in relation to the untreated control (negative control, 100%).

A dose/effect curve or time/effect curve was created from the determined values for SDS, and the exposure time (Et50) or concentration (Ec50) that causes 50% cell damage was determined. Since the samples all were only incubated in undiluted form and over a period of 48 hours, the respectively determined ΔOD was shown in percent in relation to the control.

Results a) Cytotoxicity of Samples

Figure 2:
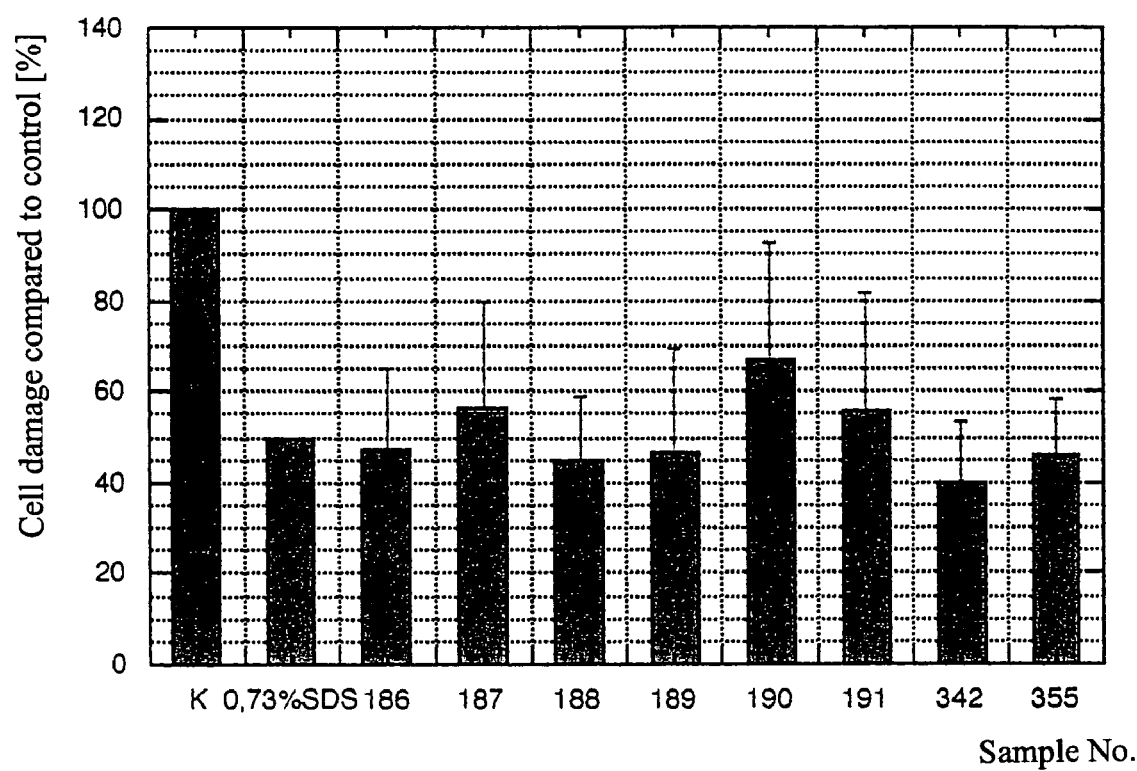
FIG. 2 is a bar graph showing the change (in percent) of the cell metabolism of skin equivalents that were incubated in the EZ4U test for 48 hours with substances to be tested.

The cell metabolism of the samples was determined photometrically after 48 hours of incubation. Using the EZ4U turnover kinetics, the respective change of the cell metabolism was determined, calculated as a percentage of the untreated control, and compared to the reference substance also run. Table 1 shows the results of this test. FIG. 2 shows the changes of the cell metabolism of skin equivalents after 48 hours of incubation of skin equivalents with different concentrations of the SDS reference substance.

TABLE 1

Change (in percent) of cell metabolism after 48 hours of incubation with the sample, in relation to untreated control (100%)

| Sample No. | AST-2000 |
|---|---|
| 0 (Control) | 100% |
| SDS 0.73% | 50% |
| 186 | 47.6 ± 17.3% |
| 187 | 56.6 ± 23.4% |
| 188 | 45 ± 13.8% |
| 189 | 46.5 ± 22.8% |
| 190 | 67 ± 25.6% |
| 191 | 55.7 ± 25.9% |
| 342 | 39.7 ± 13.6% |
| 355 | 46.1 ± 12.5% | b) Cytokine Secretion for Interleukin 1a (Il1a) as an Example

The induced secretion of cytokine Il1α was quantified by ELISA first after 24 hours and then after a subsequent, additional incubation for 24 hours with test substances in the media supernatants of the equivalents. The samples and different concentrations of SDS were used as test substances.

Secretion of Il1α After SDS Stimulation

The secretion of Il1α continuously increases in the skin model with an increase in SDS, and for a 1% SDS reaches a maximum of more than 100 pg/ml per skin equivalent. After the second incubation, the values remain overall elevated.

Secretion of Il1α After Incubation with the Samples

The Il1α secretion by the samples was relatively small (15-25 pg/ml) in the skin model after 24 hours of incubation; however, after a second incubation of 24 hours, clearly increased Il1α values could be measured.

Figure 3:
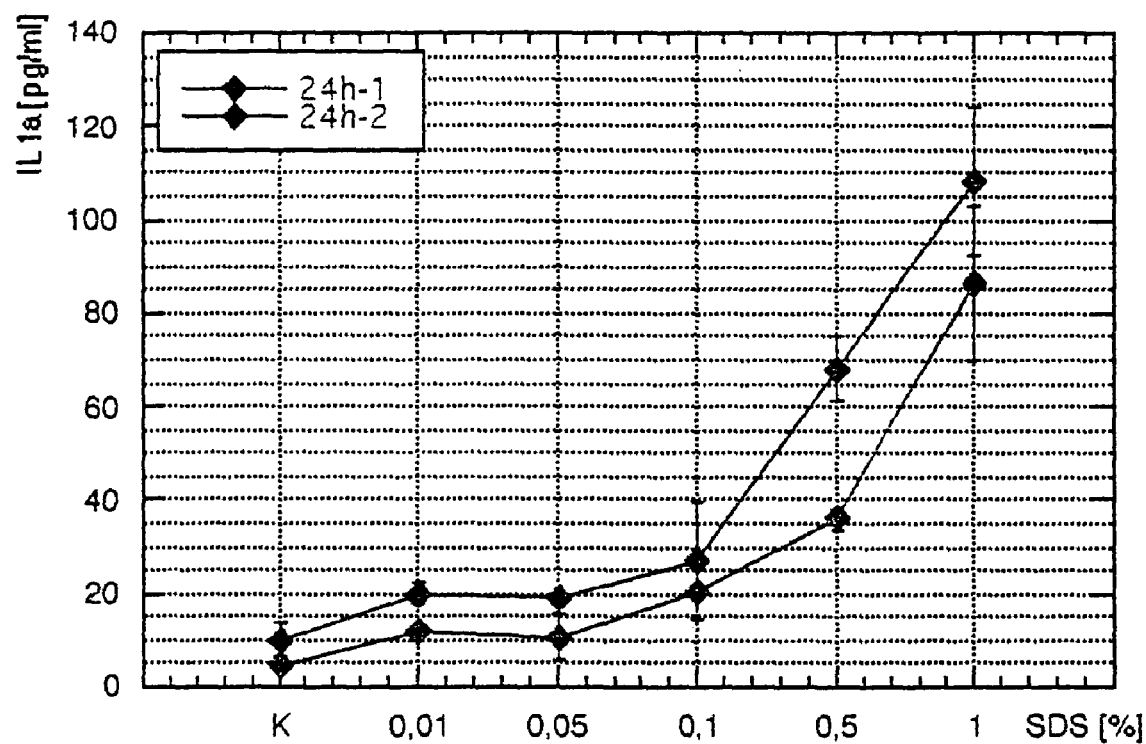
FIG. 3 in graphical form shows the changes of the interleukin 1α content in the media supernatants of skin equivalents that were incubated for 24 hours (24 h−1) and 48 hours (24 h−2) with different SDS concentrations.
Figure 4:
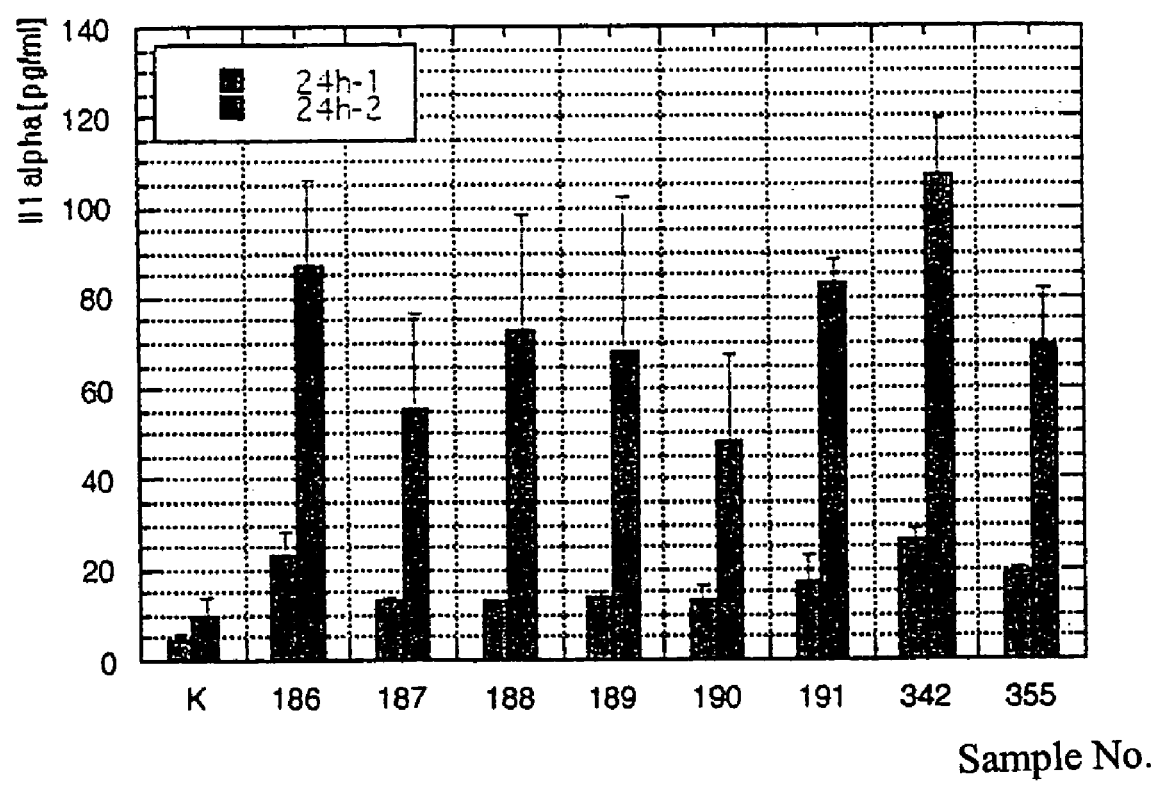
FIG. 4 shows the changes of the interleukin 1α content in the media supernatants of skin equivalents that were incubated for 24 hours (24 h−1) and 48 hours (24 h−2) with the substances to be tested.

FIG. 3 shows the results obtained with the SDS reference substance. FIG. 4 shows the results obtained with the tested samples.

c) Expression of the Prostaglandin $E_2$ ($PGE_2$) Eicosanoid

The synthesis of the $PGE_2$ inflammatory mediator was quantitatively determined by ELISA in the skin model after a first incubation for 24 hours and subsequent second incubation for 24 hours with test substances in the media supernatants of the equivalents. Samples 186-355 as well as different concentrations of SDS were used as test substances.

Secretion of PGE2 After SDS Stimulation

The synthesis of $PGE_2$ remains at an almost unchanged low level in the skin model up to an SDS concentration of 0.5%, but already rises steeply after the first 24 hours at a concentration of 1% SDS to reach up to 4000 pg/ml and more per skin equivalent. The values are practically unchanged after the second 24-hour incubation (FIG. 5).

Synthesis of $PGE_2$ After Incubation with the Samples

In the skin model, a clear $PGE_2$ synthesis was induced by the samples.

Figure 5:
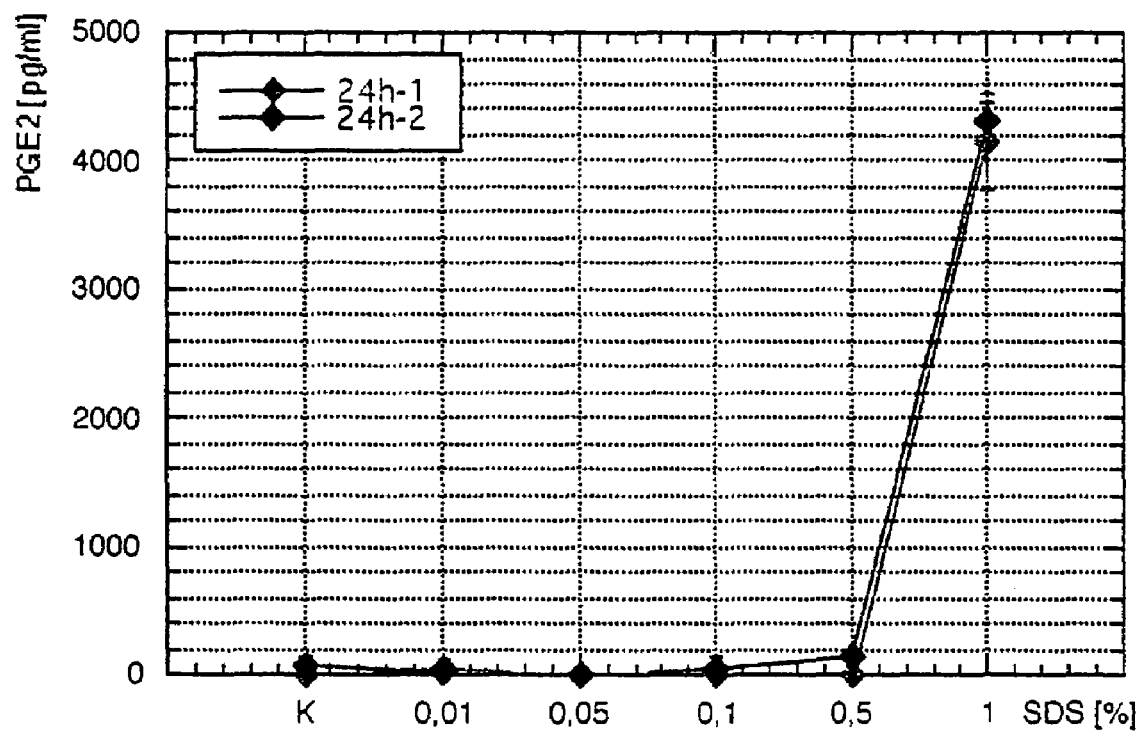
FIG. 5 shows the changes of the $PGE_2$ content in the media supernatants of skin equivalents that were incubated for 24 hours (24 h−1) and 48 hours (24 h−2) with different SDS concentrations.
Figure 6:
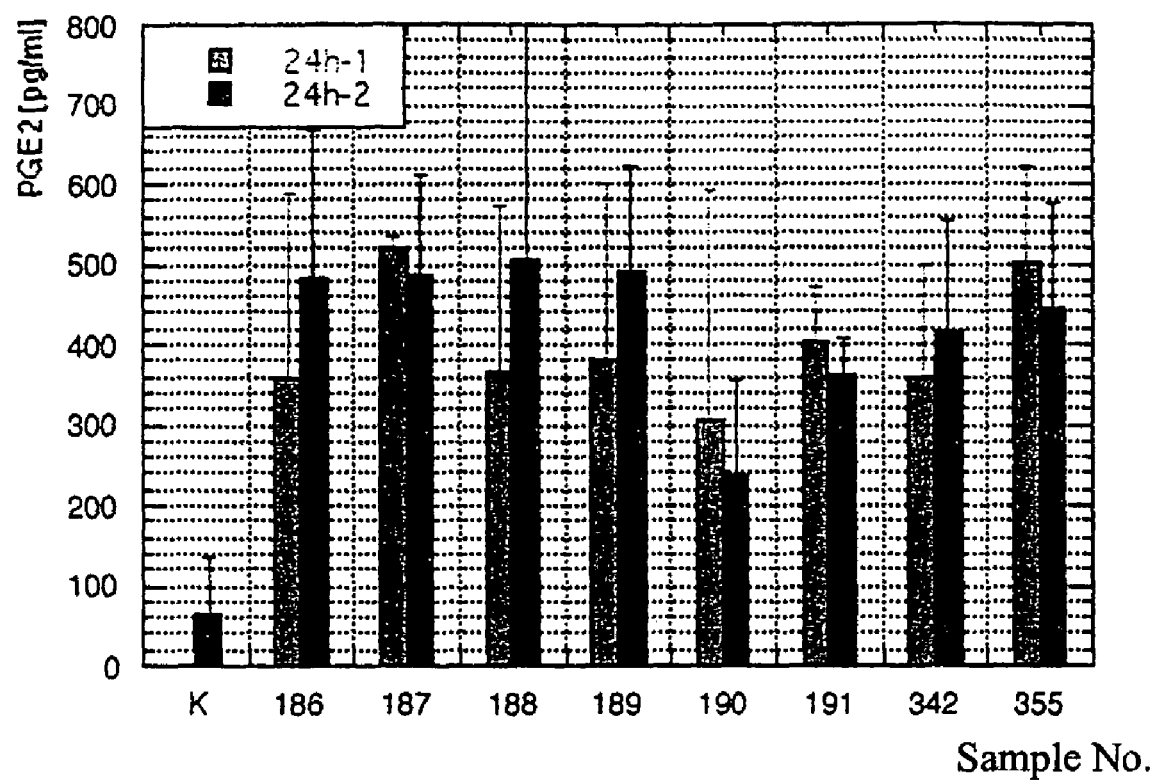
FIG. 6 in graphical form shows the changes of the $PGE_2$ content in the media supernatants of skin equivalents that were incubated for 24 hours (24 h−1) and 48 hours (24 h−2) with the substances to be tested.

FIG. 5 shows the influence of the SDS reference substance on the synthesis of $PGE_2$ in the skin equivalents according to the invention, while FIG. 6 shows the influence of the tested samples on the $PGE_2$ synthesis.

In summary, it can be stated that the skin model reacts very sensitively and differentiated to irritations. During the Il1α secretion by SDS, for example, a concentration-dependent rise can be observed. With an increase in the incubation time, the samples studied also showed a clearly increased Il1α secretion.

The study of the $PGE_2$ synthesis shows that increased secretion is triggered in the skin model by irritation. The $PGE_2$ synthesis rises substantially, for example. The values are comparable with the irritation threshold of SDS Ec50 of 0.73%. Clear values also could be measured after the samples were incubated.

d) Histological Changes of the Skin Equivalents

The morphological structure of all tested equivalents was histologically studied and evaluated after the EZ4U tests. The histological sections showed differentiated damage that was dependent on the degree of irritation. After two times 24 hours of incubation with multiple application of the sample, the studied samples showed a partially softened keratinization, loosened proliferative cell layers, and were more or less damaged.

The invention claimed is:

1. A method for producing an in vitro dermis equivalent, comprising embedding dermal fibroblasts in a three-dimensional, gel-like biomatrix containing 3.5 mg/ml up to 4.5 mg/ml of collagen in buffered serum-containing cell culture medium, whereby the biomatrix is prepared by gelling a collagen solution that has a high content of at least 90% of fresh collagen which is not denatured and not lyophilized and is prepared from rat tail tendon, and cultivating the dermal fibroblasts in such a way that an in vitro dermis equivalent in which shrinkage in at least one of the vertical and horizontal directions has been prevented and an equivalent which has a defined diameter, uniform surface and defined termination with respect to the edge of the biomatrix is obtained.

2. A method for producing an in vitro dermis equivalent according to claim 1, comprising extracting fresh rat tail collagen-containing tissue, transferring the collagen-containing tissue in acidic solution having a pH of 3 to 4, incubating the collagen tissue transferred into the acidic solution at 2 to 10° C. for 3 to 14 days, centrifuging-off undissolved collagen parts to obtain a solution having a high content of at least 90% fresh native collagen which is not denatured and not lyophilized, mixing the obtained collagen solution at 2 to 10° C. with a solution containing the dermal fibroblasts, cell culture medium, serum, and buffer, and gelling the mixed solution by increasing the temperature.

3. A method according to claim 2, wherein the cultivation is effected in the presence of a cell culture insert.

4. A method for producing a three-dimensional in vitro skin equivalent according to claim 1, comprising extracting rat tail collagen-containing tissue, transferring the collagen-containing tissue into acidic solution having a pH of 3 to 4, incubating the collagen tissue transferred into the acidic solution at 2 to 10° C. for 3 to 14 days, centrifuging-off undissolved collagen parts to obtain a solution having a high content of at least 90% fresh native collagen which is not denatured and not lyophilized, mixing the obtained collagen solution at 2 to 10° C. with a solution containing the dermal fibroblasts, cell culture medium, serum, and buffer, gelling the mixed solution by increasing the temperature, incubating the gelled mixture at 37° C., and seeding keratinocytes or other skin cell types or both onto the incubated, gelled mixture.

5. A method according to claim 4, wherein the cultivation is effected in the presence of a cell culture insert.

6. A method according to claim 1, wherein the cultivation is effected in the presence of a cell culture insert.

7. A method for producing a three-dimensional in vitro skin equivalent, comprising embedding dermal fibroblasts in a three-dimensional gel-like biomatrix obtained by gelling a collagen solution comprising 3.5 mg/ml up to 4.5 mg/ml of collagen in buffered serum-containing cell culture medium, said collagen solution having a high content of at least 90% fresh collagen which is not denatured and not lyophilized and is prepared form rat tail, subjecting said dermal fibroblasts to an at least one- to two-day submerse culture therein, seeding keratinocytes in a cell culture medium on the biomatrix, and cultivating said keratinocytes wherein a three-dimensional in vitro skin equivalent in which shrinkage in at least one of the vertical and horizontal directions has been prevented and an equivalent which has a defined diameter, uniform surface and defined termination with respect to the edge of the biomatrix is obtained.

8. A method according to claim 7, wherein the cultivation of the keratinocytes comprises at least a five to six day submerse culture and at least a 12- to 14-day airlift culture.

9. A method according to claim 7, wherein the keratinocytes have a high content of undifferentiated basal stem cells.

10. A method according to claim 7, wherein before, during, or after the seeding of the keratinocytes, other skin cell types are seeded and cultivated on the biomatrix.

11. A method according to claim 7, wherein the cultivation is effected in the presence of a cell culture insert.

* * * * *